(12) United States Patent
Breziat et al.

(10) Patent No.: US 7,980,597 B2
(45) Date of Patent: Jul. 19, 2011

(54) EXTERNAL PROTECTION FOR EXPANDABLE THREADED TUBULAR CONNECTIONS

(75) Inventors: Nicolas Breziat, Valenciennes (FR); Benoit Duquesne, Valenciennes (FR); Philippe Henaut, La Longueville (FR)

(73) Assignee: Vallourec Mannesmann Oil & Gas France, Aulnoye Aymeries (FR)

( * ) Notice: Subject to any disclaimer, the term of this patent is extended or adjusted under 35 U.S.C. 154(b) by 416 days.

(21) Appl. No.: 12/097,996

(22) PCT Filed: Dec. 15, 2006

(86) PCT No.: PCT/EP2006/069775
§ 371 (c)(1),
(2), (4) Date: Jun. 18, 2008

(87) PCT Pub. No.: WO2007/071624
PCT Pub. Date: Jun. 28, 2007

(65) Prior Publication Data
US 2008/0309069 A1 Dec. 18, 2008

(30) Foreign Application Priority Data
Dec. 23, 2005 (FR) ...................................... 05 13279

(51) Int. Cl.
*F16L 11/12* (2006.01)
(52) U.S. Cl. ...................................... 285/45; 175/325.2
(58) Field of Classification Search .................. 285/333, 285/45; 175/325.5, 325.1, 325.2
See application file for complete search history.

(56) References Cited

U.S. PATENT DOCUMENTS

| 2,546,295 A | 3/1951 | Boice |
| 3,268,275 A | 8/1966 | Laghlin |
| 3,343,890 A | 9/1967 | Homer |
| 4,380,347 A * | 4/1983 | Sable ............... 285/45 |
| 2001/0026069 A1 | 10/2001 | Linden |
| 2005/0087983 A1 | 4/2005 | Verger et al. |
| 2005/0127671 A1 | 6/2005 | Ellington et al. |
| 2006/0061098 A1 * | 3/2006 | Hovem et al. ............... 285/333 |

FOREIGN PATENT DOCUMENTS

| DE | 195 02 936 | 8/1996 |
| FR | 2 841 626 | 1/2004 |
| WO | 02 16907 | 2/2002 |
| WO | 03 059549 | 7/2003 |
| WO | WO 2004/003416 | 1/2004 |

* cited by examiner

*Primary Examiner* — Aaron Dunwoody
(74) *Attorney, Agent, or Firm* — Oblon, Spivak, McClelland, Maier & Neustadt, L.L.P.

(57) ABSTRACT

A female element of a threaded tubular connection that is fitted to undergo diametrical expansion in a plastic deformation region. The female element is disposed at one end of a tubular component and includes on its external periphery a mechanism that absorbs scratch energy of a scratching body that may come into external contact with the female element and a mechanism that retains the scratch energy absorption mechanism. The retaining mechanism is configured to prevent release of debris from the scratch energy absorption mechanism during expansion of the threaded tubular connection.

28 Claims, 6 Drawing Sheets

EXTERNAL PROTECTION FOR EXPANDABLE THREADED TUBULAR CONNECTIONS

The present invention relates to a female element of a threaded tubular connection which is fitted to undergo diametrical expansion in the plastic deformation region, provided with an external protection means and a method for determining the efficiency of said protection means.

Such a threaded connection or tubular connection may be produced by connecting threaded ends of two great length tubes or of one great length tube and a coupling to constitute in particular casing strings or tubing strings for hydrocarbon or like wells, for example geothermal wells.

Positioning such strings often causes shocks and scratches on the external periphery of the tubes which may, for example, be caused by friction of the tubes on the well walls when it is not cased or on roughness created when opening up windows in the wall of the casing for producing multilateral junctions (deviated wells).

When a diametrical expansion of the tubes in the plastic deformation region is subsequently carried out in situ, for example, to improve recovery from an old well by dropping a narrow column and then expanding its diameter, or to plug any holes in a tube pierced by corrosion or by friction of drilling strings, the scratches as described above may open, in particular in the thin portions of the threaded tubular connection, and thus cause rupture of the wall of the tube at that region.

French patent FR 2 811 056 describes a threaded tubular connection that is fitted to undergo a diametrical expansion. Such a connection does not disclose any features regarding protection of the external peripheral surface of tubes which may come into direct contact with a body which can shock or externally scratch the tube.

International patent application WO 03/059549 describes a method for radial expansion in the plastic region of a threaded tubular connection which discloses the use of a tubular sleeve which before make-up is slipped on onto a free end of the female element and coupled after make-up to the male and female threaded elements to provide:
  protection of the external peripheral surfaces opposed to the threading during handling and insertion of the string into the well avoiding deterioration of said surfaces which could cause stress concentrations and result in a catastrophic rupture of the connection during subsequent plastic expansion;
  after radial expansion in the plastic region, a metal-metal seal against fluids between portions of the internal peripheral surface of said sleeve and the peripheral surfaces opposed to the threading at the male and female threaded elements.

One of the disadvantages of that method is that the sleeve has to be available on-site, which results in a loss of time and productivity when positioning the string.

Further, International patent application WO 2004/003416 discloses a threaded tubular connection for expansion in the plastic region comprising a first male element and a second female element which are mutually connected by make-up at least one of first and second elements of which comprises a non threaded lip which extends between the threading and the free end of at least one of said elements and which has a sealing surface which are capable of coming into sealing contact with the facing surface of the other element after expansion. Said connection comprises a tubular sleeve slipped before make-up onto the second female element onsite and positioned so that it extends essentially axially facing said sealing surface. Said sleeve is intended to improve the performances of the sealing surfaces disposed on the threaded elements of the connection but also intrinsically provides an external protection of the male and female elements, and in particular their thin ends. That sleeve may be produced without overlapping the female element and may be coupled only to that element, in particular by bonding.

The aim of the present invention is to provide a further means for externally protecting a female element which enables not only to ensure non-propagation of rupture initiators such as scratches or shocks in the female element, but also to ensure that said protection means is retained integrally before, during or after expansion, preventing all or part of it from falling to the bottom of a well, for example.

The invention concerns a female element of a threaded tubular connection which is fitted to undergo diametrical expansion in the plastic deformation region disposed at one end of a tubular component. The tubular component may in particular be a tube several metres in length or a relatively short coupling (100 to 500 mm) for connecting two great length tubes.

In accordance with a principal characteristic, the female element comprises, on its external periphery:
  a means for absorbing the scratch energy from a scratching body which may come into external contact with the female element;
  a means for retaining said scratch energy absorption means intended to prevent the release of debris from said scratch energy absorption means during expansion of the threaded tubular connection.

Henceforth, said scratch energy absorption means will be termed the "absorption means".

In accordance with an advantageous implementation, said absorption and retaining means are disposed substantially starting from the free end of the female element.

Advantageously, said absorption and retaining means do not extend axially beyond the free end of the female element.

Advantageously, said absorption and retaining means extend axially over at least the length of the female element.

Advantageously again, said absorption and retaining means are continuous over the entire circumference of the female element.

Advantageously, said absorption and retaining means are disposed in the plant on the female element during the manufacturing of the female element.

In one embodiment, said absorption means is a layer deposited on the surface of the female element.

Preferably, said deposited layer is obtained using a dry deposition method.

Advantageously, said absorption means is formed from metal or a metal alloy selected from ductile metals and alloys.

In an advantageous embodiment, said retaining means is a coating produced on said absorption means.

Preferably, said retaining means axially overlaps said absorption means so as to overlay the female element over at least a portion thereof.

Said retaining means advantageously comprises a synthetic plastic material preferably selected from elastomers.

Preferably, the total thickness of the absorption means/retaining means assembly is in the range 0.5 to 5 mm.

The adhesion between said absorption means and said retaining means and/or the external periphery of the female element is advantageously improved by applying an adhesion priming paint to said absorption means and/or the portion of said external periphery of the female element in contact with said retaining means.

The invention also concerns a threaded tubular connection comprising a female element in accordance with the invention and a male element which is fitted to cooperate by make up with said female element. In accordance with the invention, said male element is not in contact with said absorption and retaining means.

A method for determining the efficiency of an absorption means disposed on a female element of a threaded tubular connection has also been developed by seeking to reproduce the typical scratch conditions in a well in a reproducible manner.

The method for determining the efficiency of said absorption means of the invention consists of disposing on a scratch test device a tube portion of a given length of a tubular component provided externally with an absorption means.

Said scratch test device comprises:
- a tool for producing scratches which is fitted to come into external contact with said tube portion;
- a means for applying a given radial load to said tool, the load being directed normal to said tube portion and towards said tube portion or for applying a given radial load to said tube portion, in which case the load is directed normal to said tool and towards said tool;
- a means for relative translational displacement of said tube portion with respect to said tool parallel to the axis of said tube portion.

Next, a given load regime is exerted between said tool and said tube portion for a given time period during which said tube portion is subjected to a relative axial displacement with respect to said tool at a given relative displacement rate regime during said given time.

At the end of the scratch test, the presence or not of a scratch is determined on said tube portion beneath said absorption means.

Advantageously, said relative displacement rate regime and/or said load are constant for a substantial fraction of the duration of the test.

In order to quantitatively determine the scratch energy absorption capacity of the absorption means, the maximum depth of the scratch is preferably measured by determining the transverse profile of the scratch.

To determine the overall efficiency of an external protection of a female element of an expansible threaded connection, said tube portion may be externally provided with a means for retaining said absorption means and be subjected after the scratch test to diametrical expansion by a given percentage in the plastic deformation region.

Cracking or not of the tube portion is then observed and the presence or not of debris and/or pieces of said absorption and/or retaining means is also ascertained.

Other characteristics and advantages of the invention will become apparent from the following detailed description and from the accompanying drawings, in which.

Figure 4A:
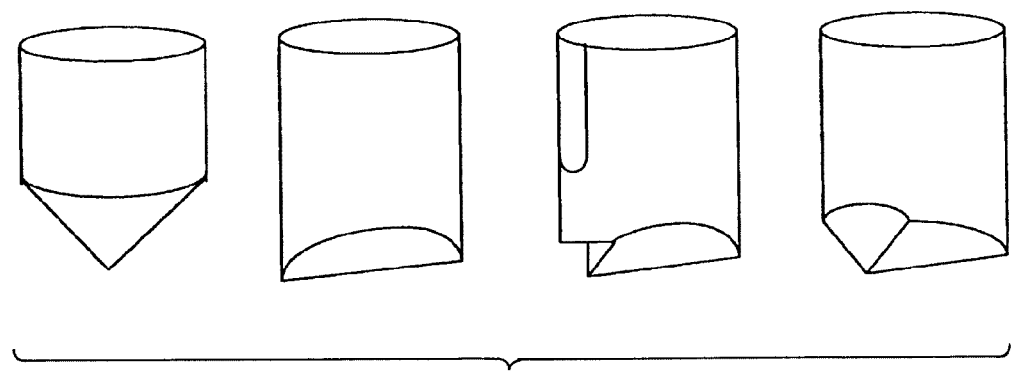
Figure 4B:
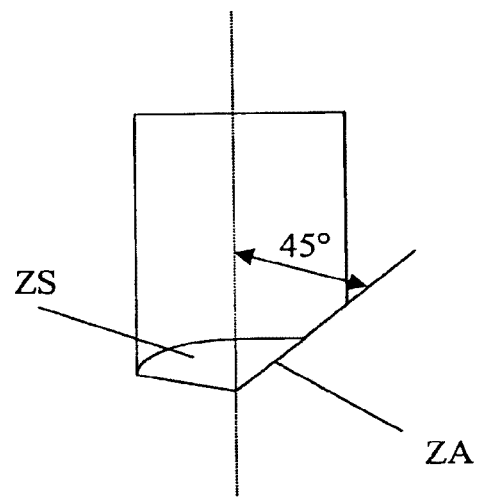

FIGS. 4*a* and 4*b* show different forms of scratch-producing tools.

Figure 5:
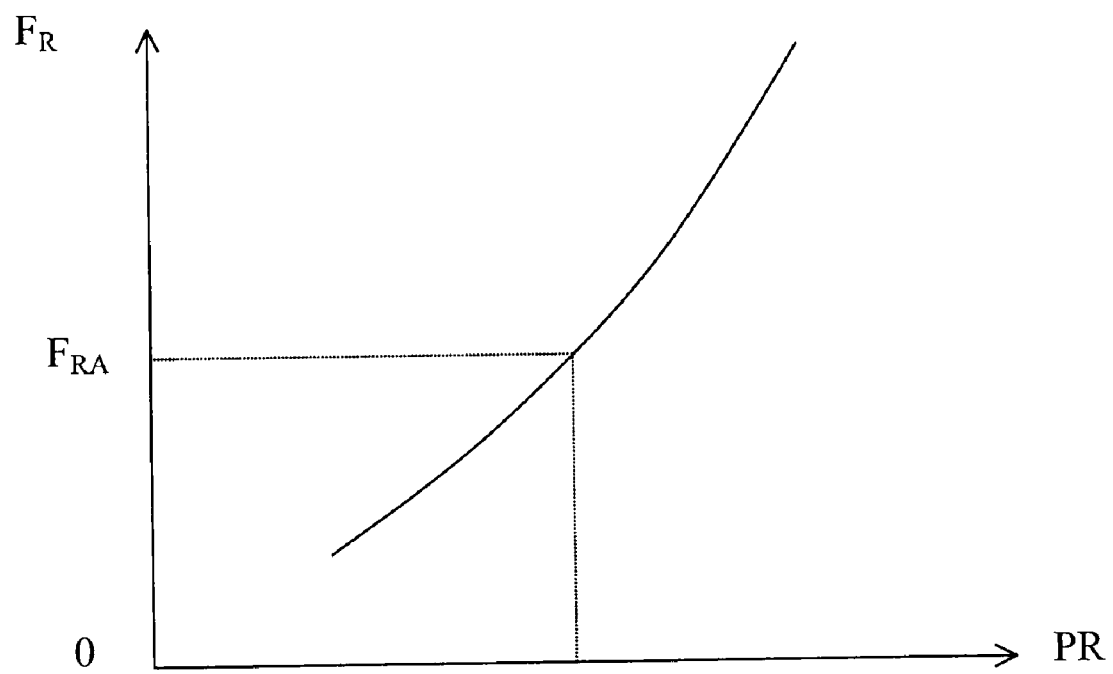
Figure 6:
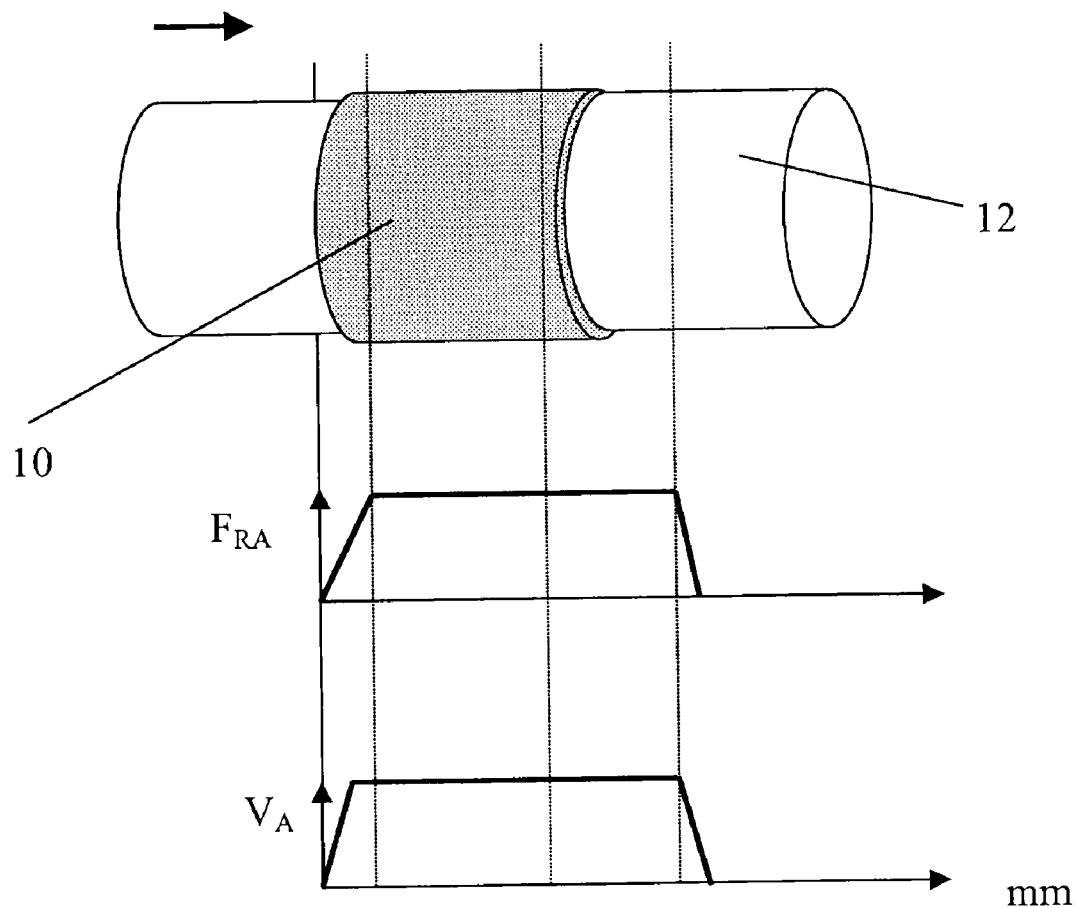
Figure 7:
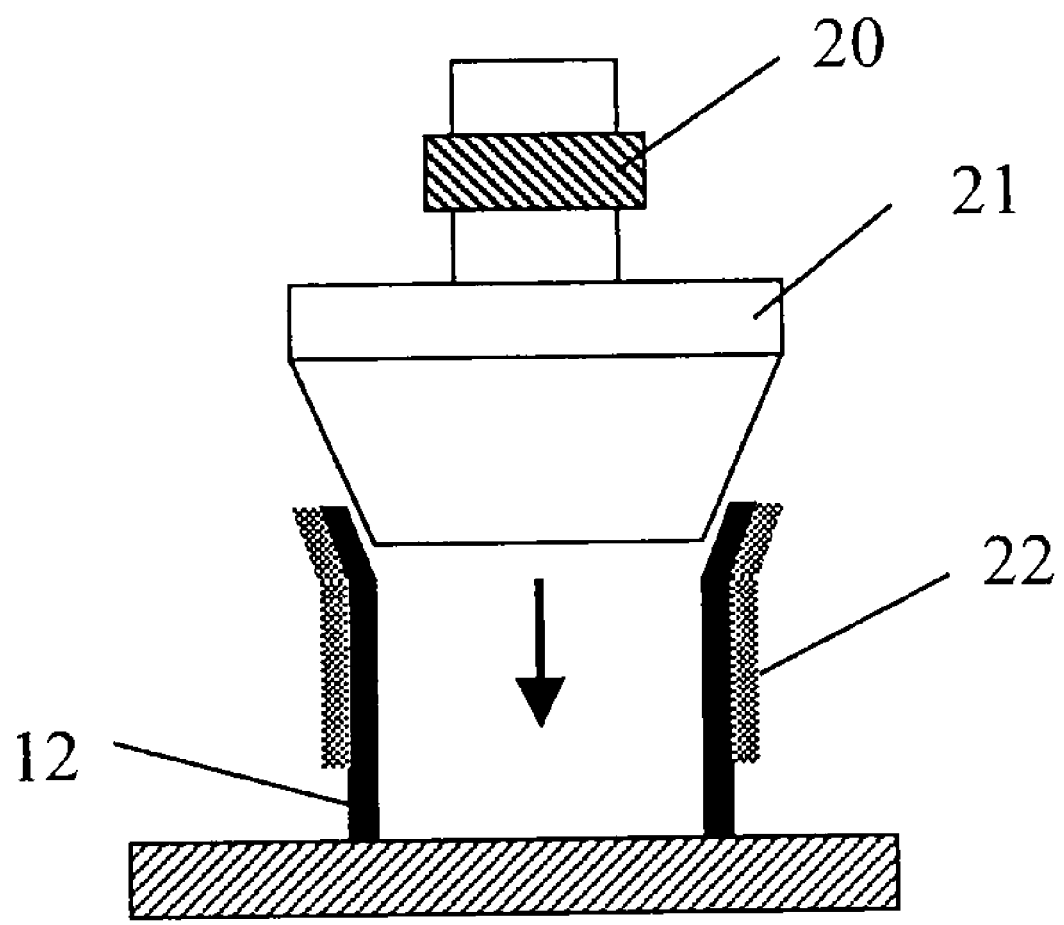

FIG. 4*b* is a preferred shape of the invention;

FIG. 5 shows a load/scratch depth calibration curve using the tool shown in FIG. 4*b*;

FIG. 6 is a diagrammatic representation of the scratch test of the invention;

FIG. 7 shows an expansion test device in accordance with the invention.

The description below and drawings referred to therein are simply examples of embodiments of the present invention and do not limit the scope thereof to these examples.

Figure 1:
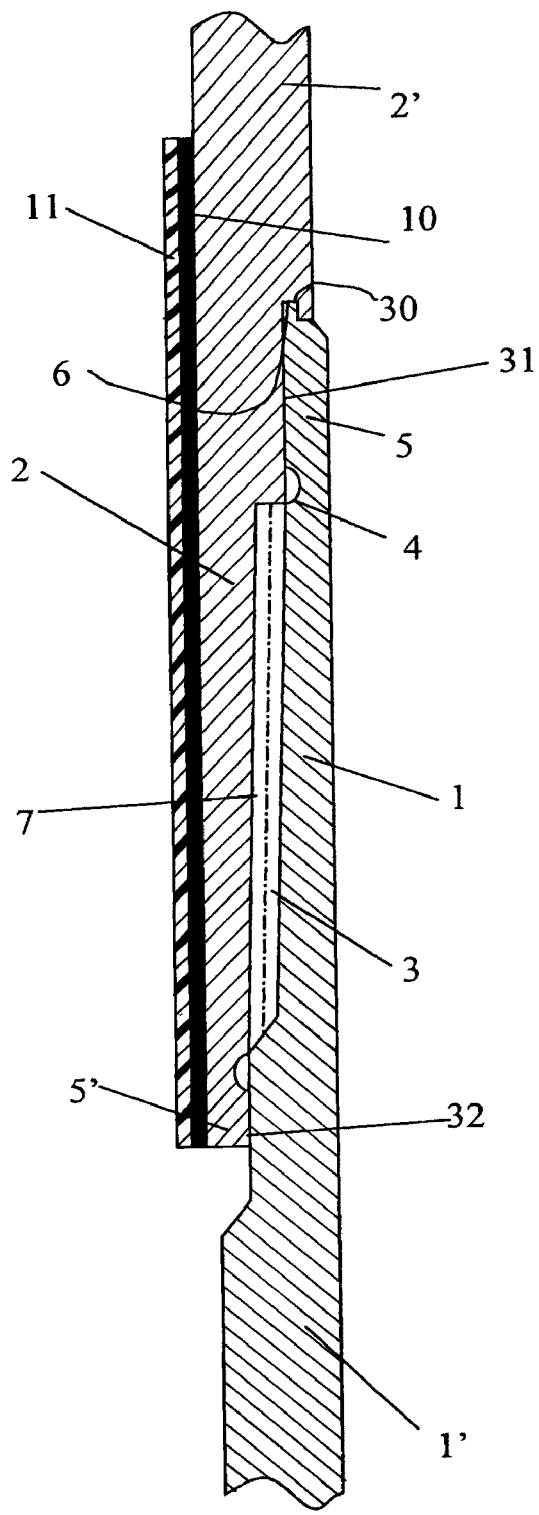
FIG. 1 shows an expandable threaded tubular connection, provided with an external protection means in accordance with the invention.

FIG. 1 shows a threaded tubular connection as described in International patent application WO 2004/003416 in the made up state abutted before any diametrical expansion operation.

It comprises a male element 1 disposed at the end of a first tubular element 1' and a female element 2 disposed at the end of a second tubular element 2'.

The female element 2 is provided with an absorption means 10 and a retaining means 11 for said absorption means 10.

Said means 10 and 11 do not extend axially beyond the free end of the female element 2 and consequently are not in contact with the male element 1.

The male element 1 comprises a tapered male threading 3 and is extended towards its free end by a non threaded portion constituted by a groove 4 and a lip 5 and terminates in a male annular free end surface 6.

The female element 2 comprises a female threading 7 homologous with the tapered male threading 3 and a non threaded portion forming a recess 8 to correspond with and cooperate with the lip 5 of the male element 1 and the male annular free end surface 6, this latter being in axial abutment against a shoulder surface 30 of the recess 8.

As explained in International application WO 2004/003416, during diametrical expansion in the plastic region, fitting the male annular free end surface 6 via the corresponding surface 30 of the recess 8 of the female element enables to radially hold the male annular free end surface 6, and a sealed radial interference fit is obtained between a portion of the external peripheral surface of the lip 5 and a portion of the internal peripheral surface 31 of the recess 8 of the female element 2.

The female element 2 extends beyond the threading via a lip 5' a portion of the internal peripheral surface 32 of which is radially interference fitted against a portion of a corresponding external peripheral surface located at the base of the male element 1 after make-up and/or after expansion.

In variations which are not shown, it is possible, to have for example:
- other shapes for the end surfaces
- a central abutment or an abutment at the female end rather than at the male end,
- no sealing surface or only one sealing surface on each element,
- different types of threading (straight with one or more stages, tapered with several stages, etc).

Absorption means 10 and retaining means 11 are disposed in the plant on the female element 2, during the manufacturing of said female element, which has the advantage of being carried out in a clean environment and saving time on-site by avoiding having to mount said absorption means 10 and retaining means 11 during positioning of the string.

A further advantage of positioning said absorption means 10 and retaining means 11 in the plant, during the manufacturing of said female element, is the external protection it affords to said female element 2 before make-up, the exterior periphery of which may be exposed to shocks during handling of the tubes and/or their transport.

Figure 2:
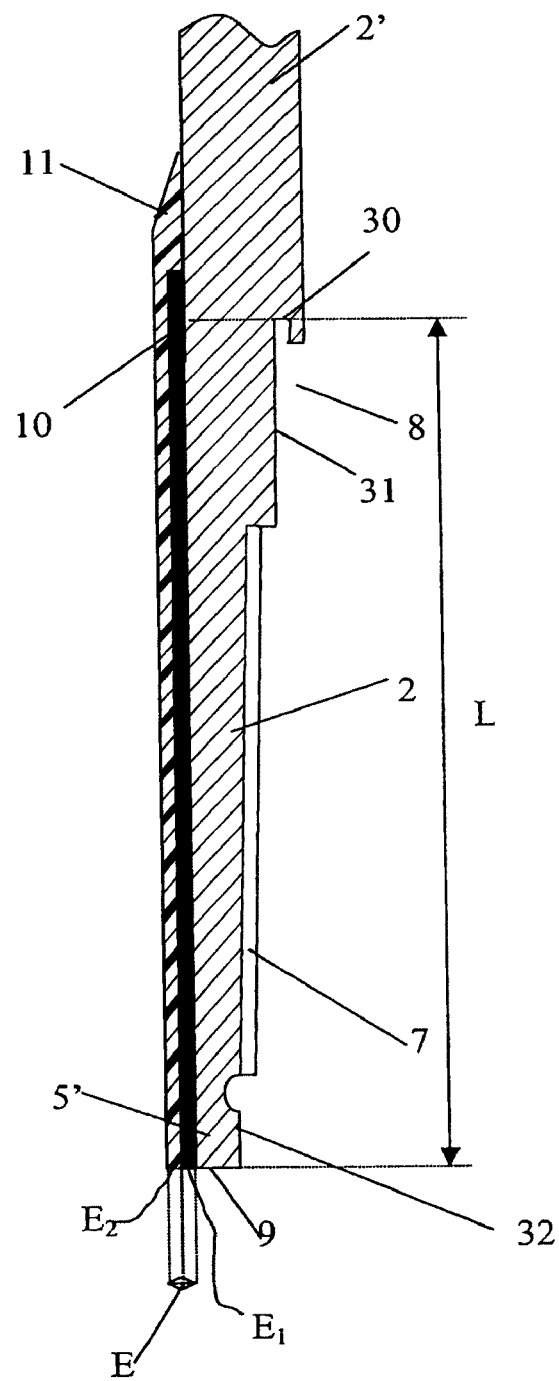
FIG. 2 shows an embodiment of the invention of a female element of a threaded tubular connection of the type shown in FIG. 1.

FIG. 2 shows the female element alone provided with absorption means 10 and retaining means 11 disposed in accordance with a particular embodiment of the invention.

The principle of this particular embodiment of the invention illustrated in FIG. 2 is the superimposition of the absorption means 10 and retaining means 11 of said absorption means 10.

The absorption means 10 and retaining means 11 are disposed substantially starting from the free end 9 of the female element without overlapping axially and cover the entire circumference of the female element 2.

Advantageously, the absorption means 10 and retaining means 11 extend axially slightly beyond the length of the female element 2.

This means to say that the axial length of the absorption means 10 and retaining means 11 is slightly greater than the length of the tube lost during make-up L (make-up loss). The length L is, for example, 50 to 200 mm depending on the external diameter of the second tubular element 2' if this is in the range 50 mm to 340 mm.

The absorption means 10 enables to prevent the propagation of cracks in the female element 2 during expansion and the retaining means 11 of the absorption means 10 is fitted to remain in place during expansion without flaking or allowing debris to escape.

Since the diameter of the female element 2 may be expanded by 5% to 25%, the anti-scratch properties of the absorption means 10 are not required during expansion or on continuing service in the well. Hence, the absorption means 10 may crack during or after expansion, or degrade from a more general viewpoint.

The total thickness E of the absorption means 10 and retaining means 11 is thus selected so as to be neither too weak to prevent the scratches from traversing the absorption means 10, nor too strong to avoid a loss of adhesion of the retaining means 11 on the female element 2, an excessive diametrical dimension and an excessive additional expansion load with respect to that of the tube (an excess load of 10% or less is desirable).

The total thickness E of the absorption means 10 and retaining means 11 is preferably in the range 0.5 to 5 mm, for example 2.5 mm.

This has an advantage over the tubular sleeve described in International application WO 2003/059549 which has a greater bulk and which necessitates an additional load during expansion.

The absorption means 10 is a layer deposited on the surface of the female element 2. This layer may be deposited by a dry process such as thermal spraying.

The principle of thermal spraying is to inject the desired material of the coating into a hot source (flame, plasma or electric arc) in the powder form or as a wire. The material is then melted into the form of fine droplets which are then sprayed under the effect of a flow of gas from the hot source to be crushed at high speed onto the substrate to be coated. These cool extremely rapidly, transferring their heat to the substrate or to previously deposited layers. Attachment to the substrate is thus extremely intimate.

Advantageously, said layer is deposited by plasma or by HVOF (high velocity oxy-fuel flame), this latter process resulting in denser, more cohesive coatings.

To encourage adhesion of said layer, the surface of the female element 2 is mechanically prepared such as by sandblasting or machining, advantageously completed by an adhesion priming sub-layer such as of the Ni—Al type.

The absorption means 10 may be formed from a metal or metal alloy selected from ductile metals and alloys, such as pure type A1 copper, copper alloys such as Cu—Al (85%-15% by weight), zinc alloys such as Zn—Al (80%-20% by weight), nickel alloys such as Ni—Al (95%-5% by weight) or Fe—Mn—C alloys (or manganese steels) with an austenitic structure.

Said ductile metals or alloys are distinguished from non ductile metallic or non metallic materials such as hard chromium, molybdenum, metallic carbides, ceramics.

In the example under consideration, said layer may be a manganese steel or a Zn—Al alloy (85%-15% by weight) and its thickness $E_1$ is 2 mm, for example, which is sufficient to prevent the formation of scratches traversing said layer, as will be seen below in the tests.

The retaining means 11 of the absorption means 10 is a coating produced on the absorption means 10 and may be obtained, for example, by producing strips applied manually to the absorption means 10, held temporarily in place by a containing envelope and, if necessary, passed through an autoclave (depending on the selected material; see below).

With the aim of guaranteeing the hold on expansion without releasing debris of the absorption means 10, the retaining means 11 axially overlaps the absorption means 10 so as to cover at least a portion of the external periphery of the female element 2 in order to fix in position any pieces of the absorption means 10 which may have broken after expansion in the plastic region.

In a variation of the invention, not shown, the retaining means 11 may completely enwrap the absorption means 10.

In the well, the threaded tubular connections are subjected not only to temperatures which may vary between 20° C. and 180° C., but also to the presence of grease, cement, mud, crude oil or gas and/or to acidic environments with concomitant corrosion risks, and to mechanical stresses of tension-compression, internal pressure, bending or twisting, which may act alone or in combination. During storage and/or transport of tubes, these latter may also be subjected to temperatures from +40° C. to −50° C.

The choice of material of the retaining means 11 is thus advantageously made from materials which ally a suitable behaviour in the temperature range under consideration, with good chemical resistance, with a high deformation capacity and with excellent adhesion to the metal.

Preferably, the retaining means 11 is formed from synthetic plastic material.

It is preferable that the synthetic plastic material has an elongation at rupture of 30% or more and preferably 40% during a tension test carried out in accordance with French standard NFT 46002 in order to keep its integrity after expansion. Highly preferably, the synthetic plastic material is selected to have an elongation at rupture of 50% or more.

In the example under consideration, the synthetic plastic material is an elastomer, for example XHNBR neoprene, and its thickness $E_2$ is 0.5 mm, for example.

In a variation, synthetic plastic materials in the thermoplastic family may be used, such as polypropylenes, polyurethanes or polyureas.

Advantageously, a thermoplastic material is selected which has a melting or softening point of 150° C. or more, highly advantageously 180° C. or more.

The synthetic plastic material may also be reinforced with particles or fibres of hard material as for instance glass fibres or powdered silica.

It is preferable for the synthetic plastic material to have a minimum adhesion to the female element 2 and the absorption means 10 of 15 N/mm at 23° C. in accordance with the standard NF-A 49-710.

To improve adhesion between the absorption means 10 and the retaining means 11 and/or the external periphery of the female element 2 in contact with the retaining means 11, an adhesion priming paint may be applied to the absorption means 10 and/or the external periphery of the female element 2 in contact with the retaining means 10.

Said adhesion priming paint is, for example, a solvent-based paint based on products sold by KALKER with reference numbers W189 or W190.

The invention also concerns a method for determining the efficiency of the absorption means 10 which employs a particular scratch test completed, if necessary, by an expansion test.

The scratch test of the invention is carried out using a particular scratch test device.

Figure 3:
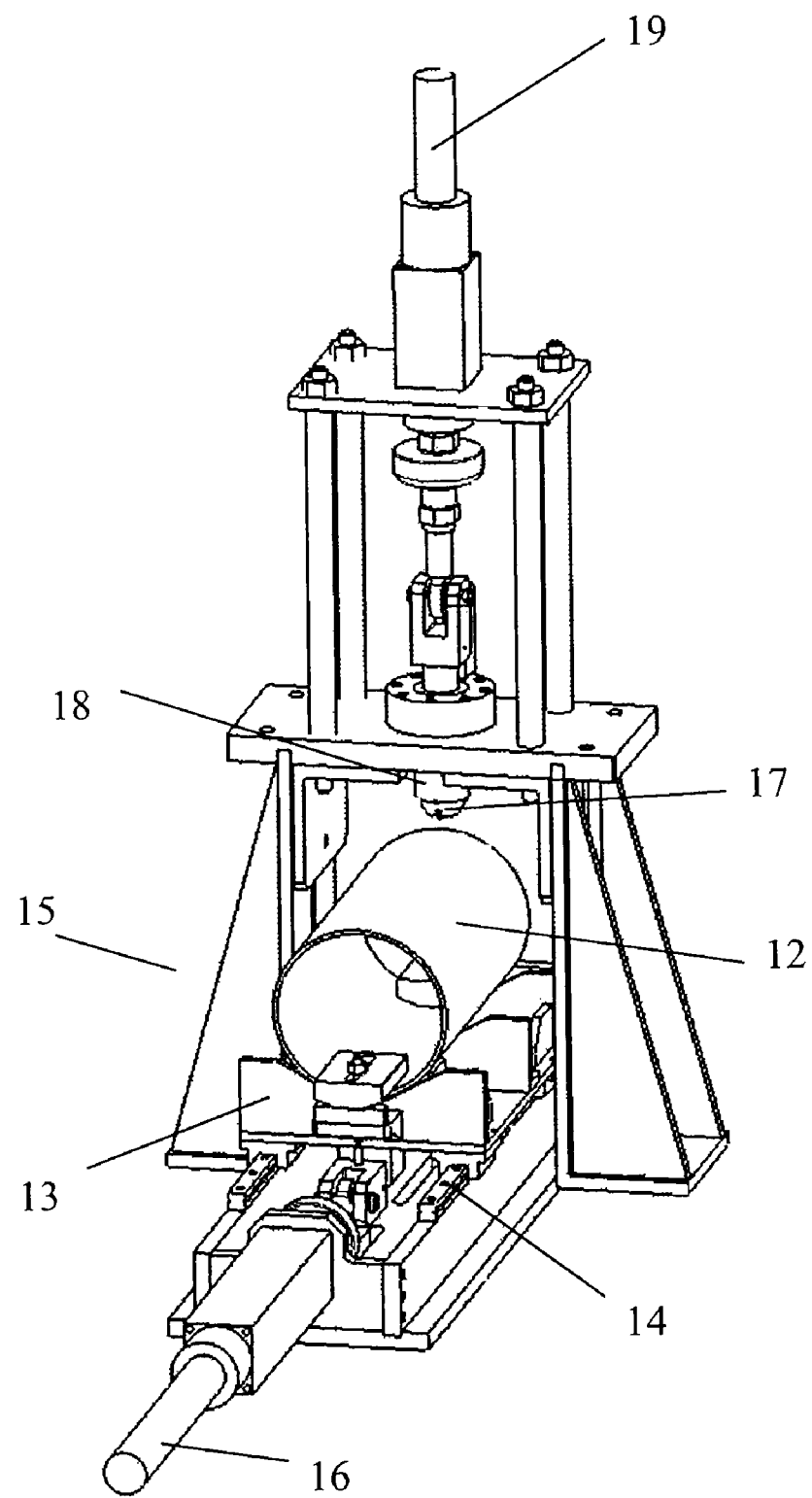
FIG. 3 shows a scratch test device in accordance with the invention.

An example of a scratch test device which enables to reproduce a scratch on a tubular element such as that which occurs in wells is illustrated in FIG. 3. A given length of a second tubular element 2' with dimensions corresponding to the female element 2 (same external diameter and same thickness) termed a tube portion 12, externally coated if necessary with absorption means 10, is positioned on a carriage 13 rolling on tracks 14 fixed on the frame 15 of the device and coupled to the movable rod of a horizontal displacement cylinder 16 parallel to the axis of said tube portion 12. Above the tube portion 12 is a scratch-producing tool 17 disposed substantially normal to the tube portion 12 in a tool holder 18 connected to the movable rod of a vertical displacement cylinder 19 enabling to apply a radial load $F_R$ to the scratch-producing tool 17 for a given period during displacement of the tube portion 12 at the axial speed of the test.

The radial load $F_R$ applied to the scratch-producing tool 17 is directed normal to the tube portion 12 and towards the tube portion 12.

In a variation (not shown), the vertical displacement cylinder 19 may be connected to the tube portion 12 so as to apply the radial load $F_R$ to the tube portion 12 towards the scratch-producing tool 17 and the horizontal displacement cylinder 16 may displace the scratch-producing tool 17 in translation along the axis of the tube portion 12.

The scratch-producing tool 17 is disposed substantially normal to the tube portion 12 and has a zone of attack ZA which is that via which the scratch-producing tool 17 penetrates into the tube portion 12, and an exit zone ZS opposed to the zone of attack ZA.

FIG. 4a shows several possible geometric shapes for the scratch-producing tool 17.

Preferably, a generally conical shape is selected with an angle of attack of 45°, as shown in FIG. 4b, and the hardness of the material is 60 HRC or more (rapid steel or carbide steel).

The maximum depth of the scratch PR may be measured after the scratch test using micro geometric surface sensing through the scratch using a profilometer. This sensing may be carried out at various locations along the scratch to provide a very accurate determination of the maximum depth PR of the scratch.

In order to reproduce the scratch conditions in a well, a maximum scratch depth PR is determined on the tube portion 12 not coated with the absorption means 10 using said test device. A calibration curve is obtained giving the maximum scratch depth PR as a function of the radial load $F_R$ applied to the uncoated tube portion 12. This determination may be made, for example, at a rate of displacement of the tube portion 12 of 400 mm/sec with the scratch-producing tool 17 having the generally conical shape shown in FIG. 4b.

FIG. 5 shows said calibration curve which enables to correlate the radial load $F_R$ with a maximum scratch depth PR obtained on a tube portion 12 without the absorption means 10.

The suitable radial load $F_{RA}$ to be applied to the tube portion 12 externally provided with the absorption means 10 can be deduced therefrom to obtain a scratch under conditions equivalent to those of the uncoated tube portion 12 with the given axial rate of the test.

The method for determining the efficiency of the absorption means 10 of the invention thus consists of carrying out a scratch test on the test device as described above, with applying the suitable radial load $F_{RA}$ on the tube portion 12 externally provided with the absorption means 10.

The suitable radial load $F_{RA}$ is, for example, 80 DaN to obtain, in a tube portion 12 of low alloy steel with a yield strength of more than 550 MPa and not provided with said absorption means 10, a maximum scratch depth PR of 600 μm at said axial test rate of 400 mm/sec, which represents extremely severe scratch conditions compared with those generally encountered in the well.

Clearly, less severe scratch conditions may be selected which are similar to the conditions actually encountered in the well.

FIG. 6 represents the variation in applying the suitable radial load $F_{RA}$ during relative axial displacement of the tube portion 12 externally provided with the absorption means 10. During a substantial fraction, at least 50% (for example 90%), of the scratch test, the suitable radial load $F_{RA}$ is constant.

FIG. 6 also shows the variation in the axial rate of the test $v_A$ during relative axial displacement of the tube portion 12 provided externally with absorption means. During a substantial fraction (at least 50%) of the scratch test, for example 90%, the axial rate of the test $v_A$ is constant.

At the end of the scratch test as described in the invention, the maximum depth of the scratch PR obtained on the tube portion 12 externally provided with absorption means 10 is determined in order to determine the traversing nature or not of said scratch beneath the absorption means 10.

Table 1 below shows the results of the scratch test on the absorption means 10 of the invention for different materials tested and applied as a layer of thickness 2.5 mm.

TABLE 1

Results of scratch tests for different materials for the absorption means 10 tested with a suitable radial load $F_{RA}$ of 80 DaN and an axial rate of 400 mm/sec.

| Absorption means | Type of absorption means | Scratch depth (mm) | Traversing scratch |
|---|---|---|---|
| Zn—Al (85%-15% by weight) | Metal | 1.9 | No |
| Cu—Al (90%-10% by weight) | Metal | 1.1 | No |
| Ni—Al (95%-5% by weight) | Metal | <1 | No |
| Manganese steel | Metal | 1.1 | No |
| Tungsten carbide | Ceramic | 1 | No |

TABLE 1-continued

Results of scratch tests for different materials for the absorption means 10 tested with a suitable radial load $F_{RA}$ of 80 DaN and an axial rate of 400 mm/sec.

| Absorption means | Type of absorption means | Scratch depth (mm) | Traversing scratch |
|---|---|---|---|
| Endoprene 8500 | Thermoplastic (polyurethane) | >2.5 | Yes |
| Eurokote 4820 | Cross-linkable (epoxy) | >2.5 | Yes |
| K8161 | Elastomer (XHNBR) | >2.5 | Yes |
| Reference (uncoated tube portion 12) | Low alloy steel | 0.6 | — |

It can be seen that the synthetic plastic materials are not suitable (traversing scratch) and that a thickness of said layer of 2 mm is sufficient for the other materials to absorb the scratch energy.

The test scratch of the invention is advantageously completed by an expansion test which provides information on the suitability of the external protection to the stresses of an expansion (detachment, cracks, debris, etc) and also on the additional load to be supplied to expand a threaded tubular connection the female element of which is externally protected.

FIG. 7 describes the expansion test carried out to determine the efficiency of the external protection means 22 applied to the tube portion 12 of the invention. This test consists of passing an expansion cone 21 advantageously provided with a load sensor 20 into the tube portion 12 externally coated with protection means 22 so as to enlarge the internal diameter of the tube portion 12 to a given plastic deformation. The expansion cone 21 is fixed, for example, to a ram of a vertical press with a 150 tonne capacity where the load sensor 20 is disposed at the base of the expansion cone 21 so as to measure the additional effort necessary to expand the tube portion 12 provided with its external protection means 22 with respect to expansion of the non protected tube portion 12.

The expansion tests are, for example, carried out at a rate of 15% with an expansion cone 21 with a length of 200 mm and an apex half angle of 100.

The expansion ratio is measured by the relative variation in the internal diameter of the tube portion 12.

The expansion ratio may be adapted to that of the well (generally between 5% and 25%).

Table 2 shows the results of the expansion test for different protective materials applied in a layer 2.5 mm thick.

The expansion, in the example under consideration, causes detachment of all of the tested metal layers with the emission of debris in the case of Cu—Al layers (90%-10% by weight) and Ni—Al layers (95%-5% by weight). The Zn—Al metal layers (85%-15% by weight) and manganese steel layers do not exhibit any debris after the expansion test. Only the layer of XHNBR (K8161) elastomer remains completely adhered to the tube portion 12 with no debris emission.

The measured load was similar to that of a non coated tube portion 12.

The various materials of the protection means tested on the tube portion 12 using the method described above are suitable, during expansion of the tube portion 12 provided with said protection means for not generating an additional load with respect to expansion of the uncoated tube portion 12, but they do not simultaneously satisfy the desired anti-scratch and adhesion criteria. In the light of the results of Tables 1 and 2, it appears necessary to combine a retaining means 11 with an absorption means 10 to avoid propagation of cracks in the tube portion 12 during expansion.

TABLE 2

Results of expansion tests for different materials for the external protection means tested with a degree of expansion of 15%.

| Material | Type of protection means | Appearance after expansion | Measured load (kDaN) |
|---|---|---|---|
| Zn—Al (85%-15% by weight) | Metal | Detachment, no debris | 80-85 |
| Cu—Al (90%-10% by weight) | Metal | Detachment, with debris | 80-85 |
| Ni—Al (95%-5% by weight) | Metal | Detachment, with debris | 80-85 |
| Manganese steel | Metal | Detachment, no debris | 80-85 |
| K8161 | Elastomer (XHNBR) | No detachment, no debris | 80-85 |
| Reference (uncoated tube portion 12) | Low alloy steel | — | 80-85 |

It was chosen, for example, to test, using the expansion test device described above, a tube portion 12 which had been scratched using the scratch device disclosed above and externally provided with a layer of Zn—Al (85%-15% by weight) with a thickness of 2 mm as the absorption means 10 and a coating of elastomer XHNBR (K8161) with a thickness of 0.5 mm over the Zn—Al layer and axially overlapping it on the tube portion as the retaining means 11.

After expansion and with no additional expansion load with respect to a naked tube portion, the tube portion did not exhibit any cracks and the coating assembly in the example under consideration remained in place with no debris ejection.

The invention claimed is:

1. A female element of a threaded tubular connection that is fitted to undergo diametrical expansion in a plastic deformation region, disposed at one end of a tubular component, comprising:
   means for absorbing scratch energy from a scratching body that may come into external contact with the female element, the means for absorbing scratch energy being disposed on an external periphery of the female element; and
   means for retaining the scratch energy absorption means, configured to prevent release of debris from the scratch energy absorption means during expansion of the threaded tubular connection.

2. A female element according to claim 1, wherein the scratch energy absorption means and retaining means are disposed substantially starting from a free end of the female element.

3. A female element according to claim 1, wherein the scratch energy absorption means and the retaining means do not extend axially beyond a free end of the female element.

4. A female element according to claim 1, wherein the scratch energy absorption means and the retaining means extend axially at least over the length of the female element.

5. A female element according to claim 1, wherein the scratch energy absorption means and retaining means are continuous over the entire circumference of the female element.

6. A female element according to claim 1, wherein the scratch energy absorption means and retaining means are disposed in a plant on the female element during manufacturing of the female element.

7. A female element according to claim 1, wherein the scratch energy absorption means is a layer deposited on the surface of the female element.

8. A female element according to claim 7, wherein the deposited layer is attached in an intimate way to the substrate.

9. A female element according to claim 7, wherein the deposited layer is obtained by thermal spraying or plasma spraying or HVOF spraying.

10. A female element according to claim 1, wherein the scratch energy absorption means is formed from metal or a metal alloy selected from ductile metals and alloys.

11. A female element according to claim 1, wherein the retaining means comprises a coating produced on at least the scratch energy absorption means.

12. A female element according to claim 11, wherein the retaining means axially overlaps the scratch energy absorption means so as to cover the female element over at least a portion thereof.

13. A female element according to claim 1, wherein the retaining means enwraps the scratch energy absorption means.

14. A female element according to claim 1, wherein the retaining means comprises a synthetic plastic material.

15. A female element according to claim 14, wherein the retaining means is formed from the synthetic plastic material.

16. A female element according to claim 14, wherein the synthetic plastic material is reinforced with particles or fibres of hard material.

17. A female element according to claim 14, wherein the synthetic plastic material does not have a melting or softening point of 150° C. or less.

18. A female element according to claim 14, wherein the synthetic plastic material has an elongation at rupture of more than 30% during a tensile test.

19. A female element according to claim 14, wherein the synthetic plastic material is selected from elastomers.

20. A female element according to claim 1, wherein the total thickness of the scratch energy absorption means and the retaining means is in a range 0.5 to 5 mm.

21. A female element according to claim 1, wherein adhesion between the scratch energy absorption means and the retaining means or an external periphery of the female element is improved by applying an adhesion priming paint to the scratch energy absorption means or a portion of the external periphery of the female element in contact with the retaining means.

22. A female element according to claim 1, further comprising at least one non-threaded portion comprising a sealing surface that is fitted to cooperate with a corresponding surface of a matching male element.

23. A female element according to claim 22, wherein the sealing surface is disposed on a lip at a free end of the female element or is disposed substantially at the opposite end to the free end of the female element.

24. A threaded tubular connection comprising:
   a female element according to claim 1; and
   a male element that is fitted to cooperate by make up with the female element, wherein there is no contact between the male element and the absorption and retaining means.

25. A female element according to claim 1, wherein adhesion between the scratch energy absorption means and the retaining means and an external periphery of the female element is improved by applying an adhesion priming paint to the scratch energy absorption means and a portion of the external periphery of the female element in contact with the retaining means.

26. A female element of a threaded tubular connection that is fitted to undergo diametrical expansion in a plastic deformation region, disposed at one end of a tubular component, comprising:
   a scratch energy absorption layer deposited on an external surface of the female element; and
   a retention layer that coats an external surface of the scratch energy absorption layer and that retains the scratch energy absorption layer to the female element during the diametrical expansion,
   wherein the scratch energy absorption layer and the retention layer extend axially up to a free end of the female element, but do not extend beyond the free end of the female element.

27. A female element according to claim 26, wherein the scratch energy absorption layer is a metal or a metal alloy selected from ductile metals and alloys.

28. A female element according to claim 26, wherein the retention layer is a synthetic plastic material.

* * * * *

UNITED STATES PATENT AND TRADEMARK OFFICE
CERTIFICATE OF CORRECTION

| | | |
|---|---|---|
| PATENT NO. | : 7,980,597 B2 | Page 1 of 1 |
| APPLICATION NO. | : 12/097996 | |
| DATED | : July 19, 2011 | |
| INVENTOR(S) | : Nicolas Breziat et al. | |

It is certified that error appears in the above-identified patent and that said Letters Patent is hereby corrected as shown below:

Column 9, line 61, change "100" to --10--.

Signed and Sealed this
Twenty-second Day of November, 2011

David J. Kappos
*Director of the United States Patent and Trademark Office*